(12) United States Patent
Rind

(10) Patent No.: US 11,547,757 B2
(45) Date of Patent: Jan. 10, 2023

(54) ELIMINATION OF EXOTIC PATHOGENS

(71) Applicant: Healing Oil Extracts, LLC, Gaithersburg, MD (US)

(72) Inventor: Bruce Rind, Gaithersburg, MD (US)

(73) Assignee: Healing Oil Extracts, LLC., Gaithersburg, MD (US)

( * ) Notice: Subject to any disclaimer, the term of this patent is extended or adjusted under 35 U.S.C. 154(b) by 0 days.

(21) Appl. No.: 16/698,237

(22) Filed: Nov. 27, 2019

(65) Prior Publication Data
US 2021/0154298 A1    May 27, 2021

(51) Int. Cl.
| | | |
|---|---|---|
| *A61K 36/00* | (2006.01) | |
| *A61K 41/00* | (2020.01) | |
| *A61K 36/752* | (2006.01) | |
| *A61K 36/87* | (2006.01) | |
| *A61K 36/53* | (2006.01) | |

(52) U.S. Cl.
CPC .......... *A61K 41/0057* (2013.01); *A61K 36/53* (2013.01); *A61K 36/752* (2013.01); *A61K 36/87* (2013.01)

(58) Field of Classification Search
None
See application file for complete search history.

(56) References Cited

FOREIGN PATENT DOCUMENTS

BE        850330 A  *  5/1977

* cited by examiner

*Primary Examiner* — Michael V Meller
(74) *Attorney, Agent, or Firm* — Da Vinci's Notebook, LLC

(57) ABSTRACT

The present invention includes a novel means for destroying aggressive mold in a system. A foreign target antagonist both draws and depletes defense mechanisms for the mold at which point the mold may be attacked with conventional anti-fungal preparations. A more preferred means for destroying the mold includes the post-depletion application of a mold indirect antagonist adapted to ameliorate cellular organelle deformation in the organism. In this preferred means, the organism overcomes the mold with its inherent biodefense mechanisms.

1 Claim, 13 Drawing Sheets

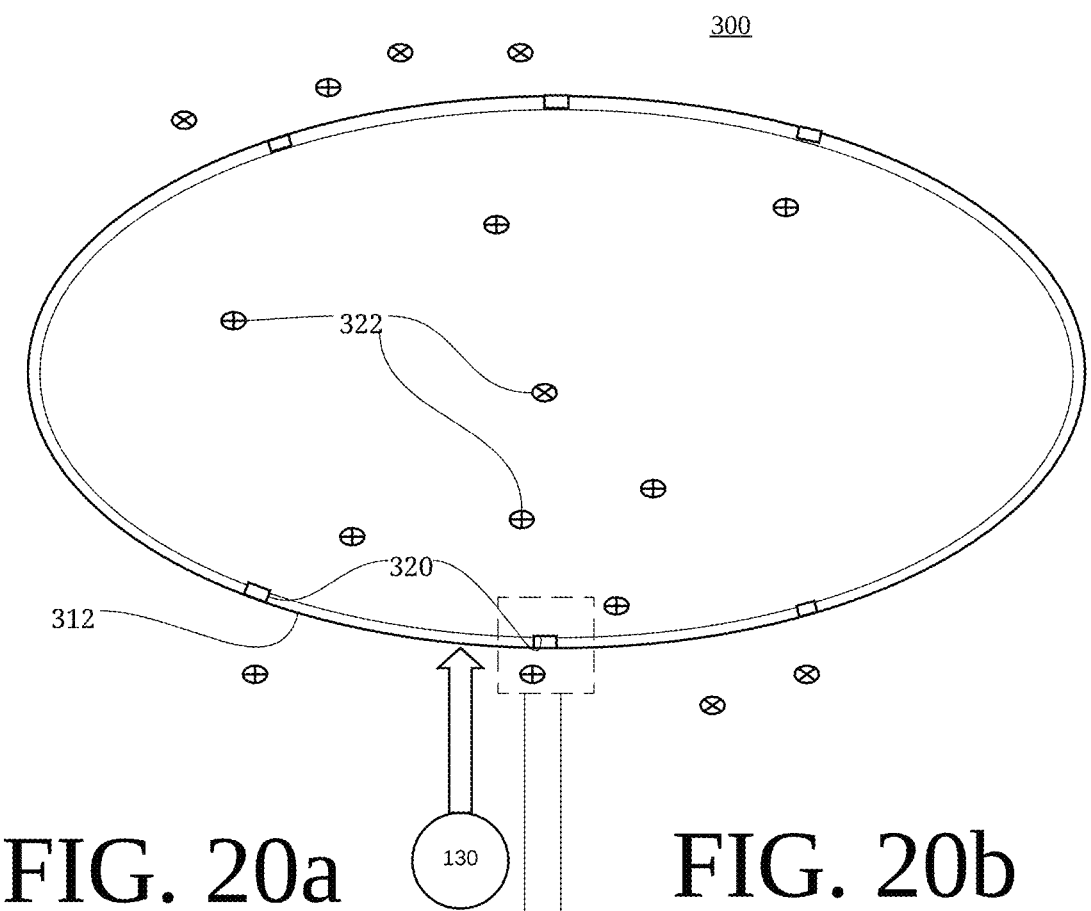
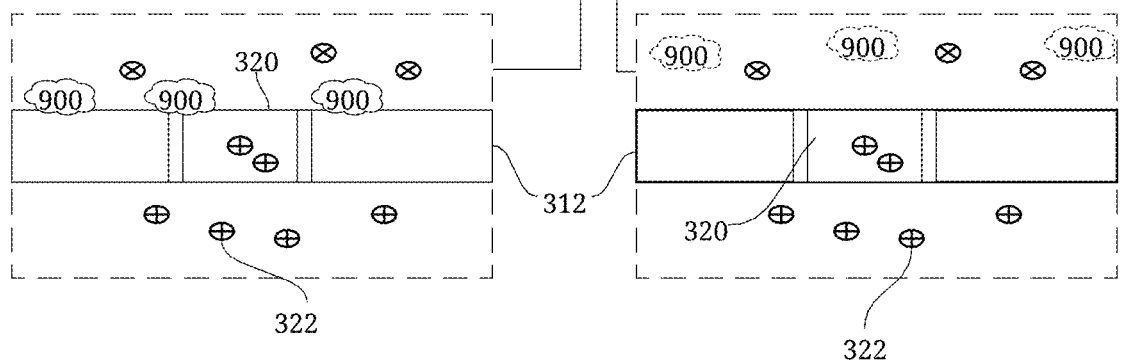

ELIMINATION OF EXOTIC PATHOGENS

FIELD OF THE INVENTION

The present invention relates to the field of health and wellness and more specifically to the field of exotic pathogen elimination.

BACKGROUND

Biotoxins include fungal (mold or yeast) toxins, and other types of toxins. The presence of biotoxins in patients shows up as several symptoms. Effects of fungal toxins cause symptoms such as coughing, wheezing, asthma, shortness of breath, sneezing, burning in the throat and lungs, sinusitis, memory loss, confusion, brain fog, and cognitive impairment may present, vision problems, eye irritation, headaches, swollen lymph nodes, ringing in the ears, dizziness, hearing loss, fatigue, muscle weakness, multiple chemical sensitivities, joint pain, muscle pain, lowered pain threshold, irregular heartbeat, seizures, depression, anxiety, irritability, psoriasis, skin irritation, fever, chills, sleep disorders, coagulation abnormalities, depletes antioxidants, alters cell membrane function, acts as potent mitochondrial toxins, alters apoptosis, may negatively affect the endocrine system, including sex hormones, thyroid function, and adrenal function, may lead to food allergies and chemical sensitivity, in some cases, POTS (postural orthostatic tachycardia syndrome) may be fungus induced, fibromyalgia and chronic fatigue syndrome (CFS) have both been associated with mycotoxin exposure. (http://www.gordonmedical.com/unravelling-complex-chronic-illness/wp-content/uploads/2014/08/Townsend-Letter-Mold-Article-1.pdf)

Detection of Mycotoxins in Patients with Chronic Fatigue Syndrome

Other conditions that may have a mycotoxin component include various cancers, diabetes, atherosclerosis, cardiovascular disease, hypertension, autism, rheumatoid arthritis, hyperlipidemia (elevated cholesterol), inflammatory bowel disease, lupus, Sj6gren's syndrome, Crohn's disease, multiple sclerosis, Alzheimer's disease, Raynaud's disease, kidney stones, and vasculitis.

Microbes have mechanisms for supporting their survival as an individual as well as a community. They produce chemical compounds that can have an adverse effect on our immune system's ability to fight them off (e.g., causing the immune system to either not recognize them or to not be able to attack them), weaken our health or ability to fight them off. Also, as with yeast, they can cause us to feed them by getting us to crave sweets. Some studies showed that oils like caprylic oil from coconut acted against fungus but were not known to decrease symptoms of fungal toxicity. Some methods for decreasing toxins include treatment with binders that directly attack the fungal population or burden as antifungals, etc. such as cholestyramine, clay, zeolite, glucomannan. Reduction of toxins can also take place by providing fungal treatment such as antibiotics, or pharmaceuticals such as Diflucan, Nizoral, Nystatin, or herbal such as Caprylic acid or oregano oil. Oregano, however can increase the toxin level by causing the fungus to release the toxins in response to the offending substance. This would transiently raise the fungal toxin level. The same (as oregano) can be said of grapefruit seed oil as this specification later details, but milder than the oregano's effect.

SUMMARY

The present invention includes a broad array of processes and systems directed to the creation of a cellular super state for purposes of health and wellness. A system of the present invention includes an artificially hyper-energized mixture composed of a photo-excited ionized carrier molecule constituent within a substantially uniform distribution of physiologically-inert solution constituent to form a base mixture. The photoexcitation results from a photon stream adapted to energize the carrier molecule beyond a ground stationary energy state. The purpose of the carrier molecule is to hold energy to apply to a group of cells in vivo or in vitro. The preferred carrier molecule, which upon energization is deemed an activated ingredient, is a group of molecules selected from the olive. The olive molecules, which can be further filtered to select preferential olive molecules, are capable of holding energy sufficient interact with cells in order to alter the state of their cellular membranes. The present invention is particularly effective at dealing with mold/fungus pathogen infections, although, the creation of the aforementioned cellular super state may be conducive to a broad range of health applications.

An interesting side-effect of mold/fungus organism infestations can be musculoskeletal tightness such that the organism's range of motion is inhibited. Of further interest is that the application of the activated ingredients of the present invention have an almost simultaneous effect in relieving musculoskeletal tension. The relief is so quick and substantial, that it can reliably be used to estimate both the existence of a mold/fungus infection and whether the organism is responsive to the treatments of the present invention.

In a process of the present invention an organism's measurable state of muscle tension/relaxation or range of motion ("ROM") is tied to the treatment. The potential of mold infection in an organism is estimated based on a musculoskeletal external motion examination of an organism. Then an ionizable carrier molecule is mixed within a physiologically-inert solution constituent to form a base mixture subsequently activated by (i) agitating said base mixture for the purpose of substantially uniform distribution of the base mixture and (ii) applying a photon stream adapted to energize the carrier molecule beyond a ground stationary energy state to generate an energized mixture. This energized mixture is introduced into the organism. The musculoskeletal motion external examination of the organism is reengaged to determine a motion difference and registering a mold infection analysis based thereon. Simply put, if the ROM remains unaltered, the treatment may not yet have taken effect or the diagnosis of mold/fungus may be in error.

Treating mold and fungus can exploit several nuances related to their life cycles and behavior. In a mold neutralization process, the present invention first drains the defenses of mold prior to attempting treatment. A mold foreign target antagonist is introduced into an organism evaluated to be infected by a mold agent. An effective level of the foreign antagonist is applied continuously or at (pulsed) intervals to allow the mold to release its chemical defenses until depletion of an appreciable amount of mold agent defense mechanisms are calculated to be exhausted. Then a mold indirect antagonist is applied to the organism adapted to ameliorate cellular organelle deformation. Although mold can be treated once its defense mechanisms are exhausted by more conventional means, it is preferred that the present invention utilize the cellular super state mentioned above to allow the body's natural, cellular defenses to engage and destroy the mold. Because mold is believed to interfere with the operation of a cellular membrane of a cell, repairing or stabilizing the membrane results in the ability to effectively attack the mold within the organism.

The cellular super state is achieved by the following process. A potential of ill-health is estimated within an organism. The activated preparation discussed above is applied to the organism, the preparation adapted to a cellular energization super state characterized by artificially elevating a voltage potential of cellular membranes within the organism. The super state is maintained for a substantial portion of a predetermined ill health period. Then a diagnosis is finally or periodically applied until the health is improving and satisfactory. The cellular super state can result in a voltage differential increase anywhere up to approximately 400% (and higher) but has been accurately measured to be approximately at least a 100% improvement.

These aspects of the invention are not meant to be exclusive. Furthermore, some features may apply to certain versions of the invention, but not others. Other features, aspects, and advantages of the present invention will be readily apparent to those of ordinary skill in the art when read in conjunction with the following description, and accompanying drawings.

BRIEF DESCRIPTION OF THE DRAWINGS

FIG. 19 is a view of an embodiment of a cell of the present invention.

FIG. 20a is a view of an embodiment of a cell of the present invention. FIG. 20b is a view of an embodiment of a cell of the present invention undergoing a transition to a cellular superstate.

DETAILED DESCRIPTION

Figure 1:
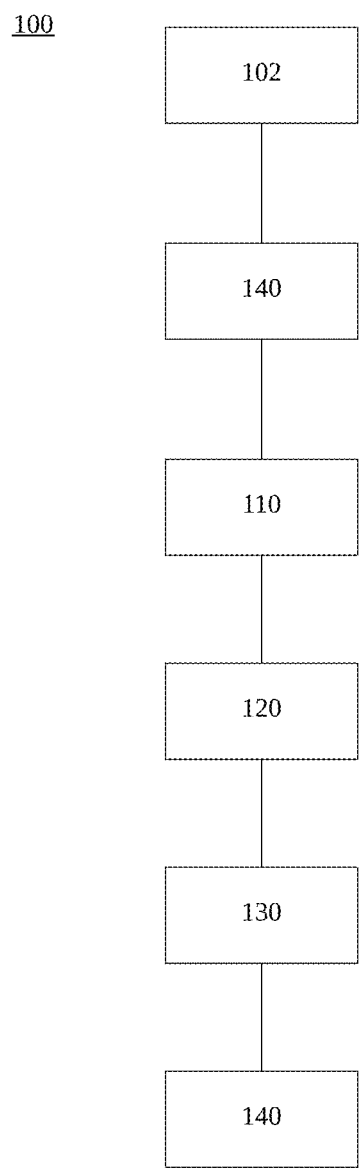
FIG. 1 is a view of an embodiment of a treatment protocol of the present invention.
Figure 2:
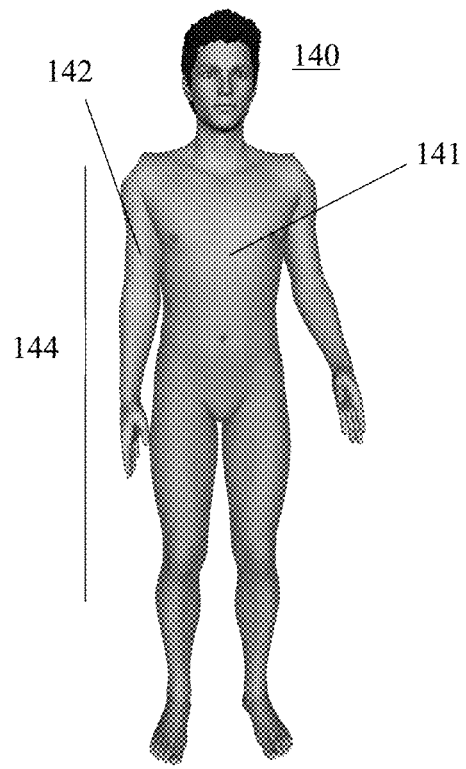
FIG. 2 is a view of range of motion physical examination parameters of the present invention.
Figure 3:
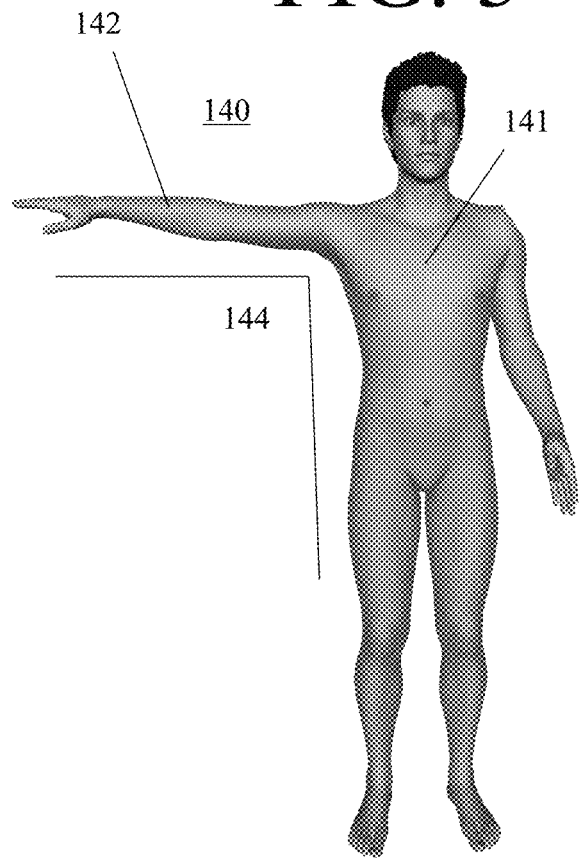
FIG. 3 is a view of range of motion physical examination parameters of the present invention.
Figure 4:
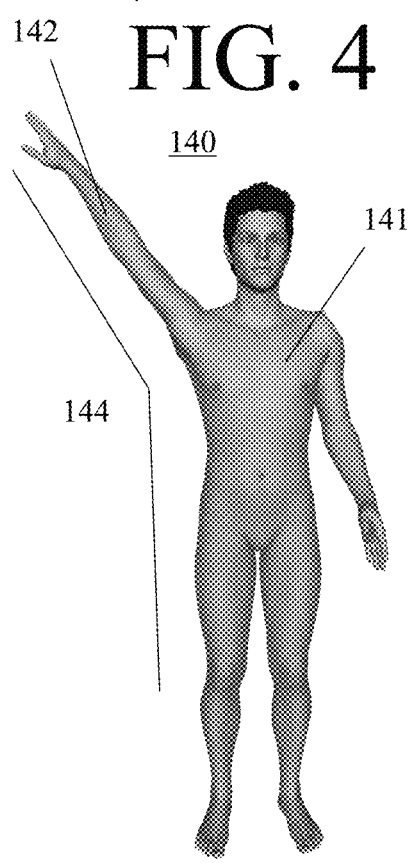
FIG. 4 is a view of range of motion physical examination parameters of the present invention.
Figure 5:
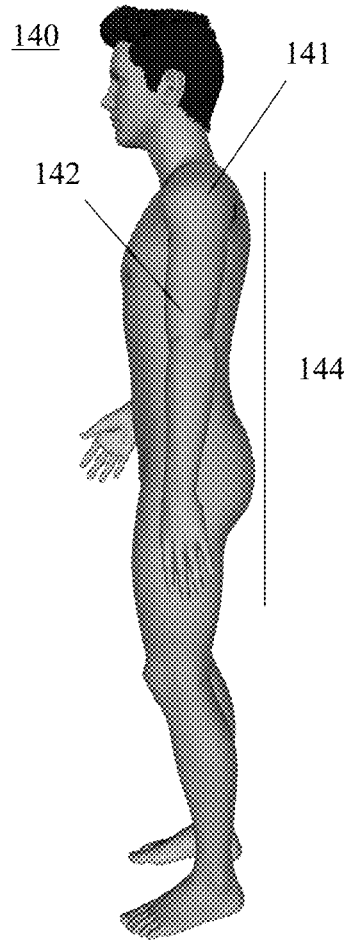
FIG. 5 is a view of range of motion physical examination parameters of the present invention.
Figure 6:
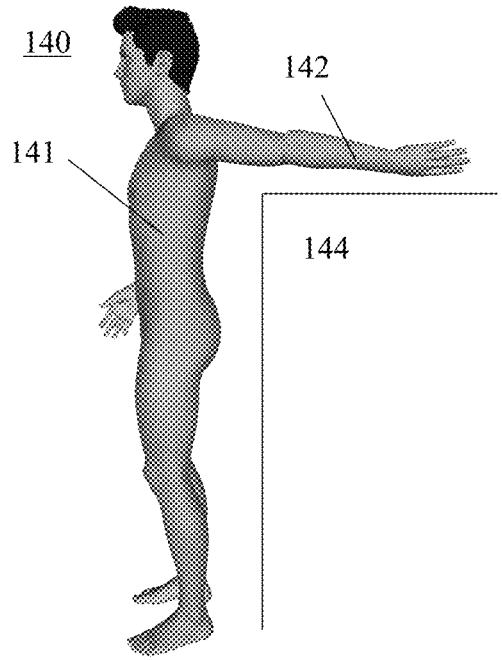
FIG. 6 is a view of range of motion physical examination parameters of the present invention.
Figure 7:
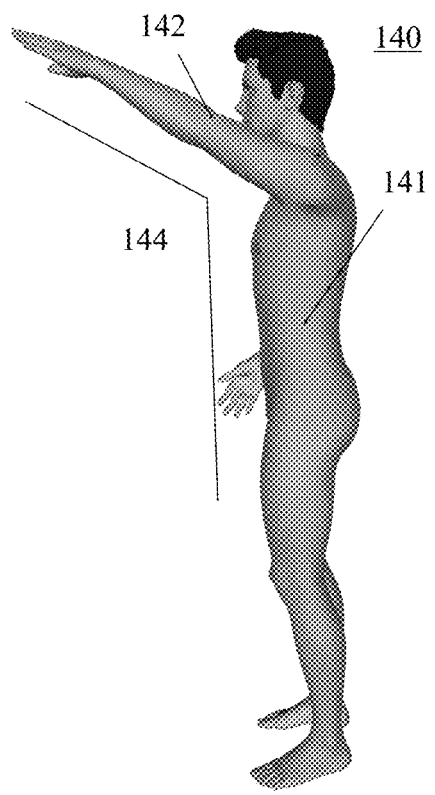
FIG. 7 is a view of range of motion physical examination parameters of the present invention.
Figure 8:
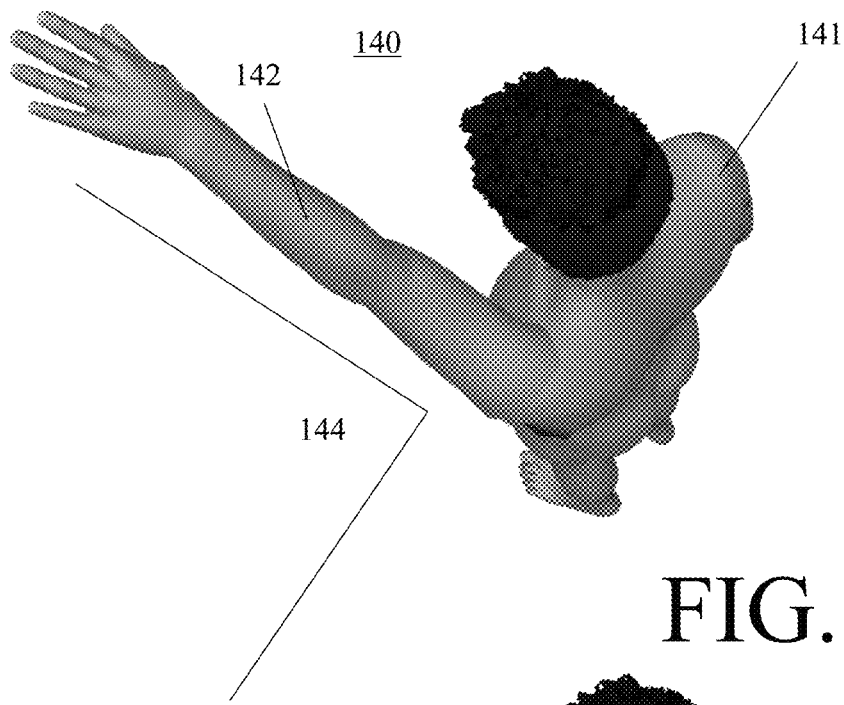
FIG. 8 is a view of range of motion physical examination parameters of the present invention.

The present invention broadly relates to a health and wellness program targeting a generally trivialized pathogen, mold. Mold is generally not recognized as a potential for ill-health and is infrequently screened by physicians in seeking a health resolution. A doctor's penchant to overlook mold isn't due to callousness or maleducation, but rather, mold simply is not the focus of much research or study. Certain types of mold related to environmental conditions, e.g. Black Mold, are the basis of a considerable body of knowledge; however black mold infections are commonly recognized, not because its infectious side effects are prominent in a patient, but because the mold is flagrantly present in a habitat or workplace. Non-black, pathogenic molds, i.e., molds capable of surviving intro vivo at 37 degrees Celsius are not merely invasive, they are omnipresent. However, the human body is adequately tolerant to substantial levels of mold; in most cases, the body and its actions deteriorate at a clip that indiscernibly fogs the mind and slows or excessively speeds the reflexes. In other cases, the effects are considerably more catastrophic.

This disclosure is not meant to be a conclusive statement on the inventor's research and study of mold. The inventor humbly reminds the reader of this document, that the inventor is merely a trained anesthesiologist with additional training in neurology, osteopathy, nutritional medicine, integrative medicine that altered the focus of his of many of his orthodox treatment protocols based on a mixture of fortuitous observations, patient study, and process of elimination. In some instances, the inventor cannot furnish an explanation suitable to quench his own curiosity and standards, much less provide a solidly scientific explanation that, taken alone, resolves all doubt. Nevertheless, the inventor has gained much acclaim in various circles and achieved results considered contrary to the notions of conventional medicine. So, it is with some apology that this document pursues the explanation of processes without a detailed, and certainly rarely conclusive, analysis of the cellular or physical mechanics underpinning the result. The following is what has been learned by the inventor (for as much accuracy as can be afforded, via time and money, by the same), and immodestly, what has been the subject of considerable entreaties of disclosure.

There is considerable support for the proposition that mold at undetectable levels finds a thriving support host in the human body. It is often found by the inventor that effects of mold are misclassified as another illness or is the basis for exacerbating the effects of another existing illness. Indeed, it is considered by the inventor to be the chief finding based on the detection capabilities available to him that mold acts as a supplement to another ailment, silently and undetectably amplifying the ailment's effects.

As an example of this principle, the inventor was once treating a young man, 16 years old, whose digestive system had shut down. He could neither eat nor drink without nausea and vomiting. Emesis resulted even from the most minute amounts of water ingestion. Several conventional medical experts were unable to ascertain the cause of the symptoms or suggest treatment. The inventor considered whether the patient had a mold problem because his symptoms appeared after his home received significant water damage subsequent to firefighters' efforts to extinguish a blazing fire at his residence. Moreover, only one of the many branches of the vagus nerve was affected (specifically, the gastrointestinal) but not the cardiac, laryngeal, or others. This type of specificity in nerve damage as well as the potential for water damage as the origin of the symptoms led the inventor to suspect the possibility of a biotoxin affecting the patient. Mold seemed the prime source of the biotoxin.

Since the patient could not even tolerate the most minute amounts of water, it was not feasible to administer an oral antifungal medication. Any IM or IV medication would have been too toxic, and there was a strong basis to believe that he would not have tolerated any medication by any method of administration. The patient was in a constant, daily cycle of being maintained by IV fluids seven days per week. He was losing weight and it was presumed that the patient's continued capacity to survive was reaching a breaking point. Some studies showed that oils such as caprylic acid from coconut acted against fungus but were not known to decrease symptoms of fungal toxicity. The inventor's previous studies showed that ideal conditions to grow mold are heat, humidity, and organic material, e.g., wood. This led the inventor to consider mold growth on olive trees in Mediterranean climates. Mediterranean areas are often warm or hot. The soil can be humid, the olive tree itself is a very slow growing tree and wood is organic material. He realized that the olive tree survives and does grow, albeit slowly. This led the inventor to consider that the olive tree has a protective mechanism that allows growth of the tree in spite of the mold. That led the inventor to consider whether the protective mechanism could be an oil. To extract olive oil with the non-commercial equipment was available to him, he chose to blend in a conventional off-the-shelf blender olives with a small amount of olive oil and allow the mixture to remain at room temperature. Although more study may be necessary to demonstrate the conclusiveness of this theory, it may be the case that heat conduction is an important aspect of energy transfer. In other words, the contact of the heated blades (based on spinning) was found helpful as a catalyst to activate oils. Of course, it is also the case that activation requires heat within a certain range to activate the oil and also not inactivate by overheating it. Separating the oil by squeezing out the oil through a cloth as well as with centrifuging it one or the other, the inventor produced a crude olive oil concentrate of at-the-time unknown proportions.

The patient received this olive oil treatment orally at a dosage of approximately one-eighth teaspoon, and the very next day he confided that he felt inclined to have, and his body successfully tolerated, a glass of water. The inventor pressed the patient to take more of the olive oil treatment as could be tolerated, and the following day, after taking about one teaspoon, the patient was capable of tolerating a quart of water. On day three, IV fluid administration was no longer needed and within two weeks he was eating a nearly normal diet with adequate fluids, solid food and calories. The patient no longer needed the IV therapy after this and over a short time, fully recovered from his illness.

This protective was then offered to other patients willing to try it. The inventor was able to observe, using the protective olive oil, changes such as improvement in skin tone (from pale or gray to pink), disappearance of neuropathic pain, and tremor in the hands (observable if looked and tested for it). The olive oil extract was later applied to patients with a strong tremor and found that in many cases, it was able to eliminate the tremor in under ten minutes. Furthermore, there were satisfactory effects related to patients' range of motion when testing muscle stiffness. Muscles had relaxed and Range-of-Motion ("ROM") improved significantly (e.g., from horizontal abduction of 0° to 90° in under 4 seconds (that is why it appears to be electrochemical, since it is too rapid to be due to a strictly chemical reason). The inventor then continued to explore different effects of the antitoxin olive oil on biotoxins.

Referring first to FIGS. 1-8, a basic embodiment of the treatment process 100 of the present invention is shown. One of the intricacies, as is believed by the inventor at the drafting of this specification, is that close relationship between muscle tension and fungus infestation. It is of further great interest that the relationship between muscle tension and fungal infestation varies rapidly when an appropriate anti-fungal solution is administered to a patient. It is believed that the relationship is so strong that muscle tension examinations to determine fungal infestation can be a routine, and immediate, member of a patient's pre-screening. Having said so, however, it is important to note that the presence of muscle tension does not immediately lead to the conclusion that fungal infestation is present, yet the because the dissipation of muscle tension is so rapidly encountered subsequent to administration of certain medicaments of the present invention, that it is believed that substantially instantaneous ROM differentiation leads to a strong conclusion that a fungal infection was both present and being adequately combatted. After successful fungal treatment, muscles stay relaxed and are no longer affected to relax with the active oil. Furthermore, they are no longer induced to be tight with the application of oregano. Upon re-exposure to mold, the muscles again tighten, are relaxed by the active oil and made to tighten by oregano oil or another fungal irritant. Also note that the tightening by oregano takes about 0.5 to 1.5 minutes to take effect because we need to wait until the mold responds to the oregano (threat) and releases its toxin and then the toxin needs to reach the target tissues (muscle, nerve, mast cell for histamine release, etc). Also, the oregano effect can be accelerated via lungs by simply smelling the oregano oil (vapors or molecules).

A patient admitted to the process 100 is first physically screened 102 for physical manifestations of a fungal infestation through musculature movement examination. The preferred basis for determination of extent of fungal infestation is a physical determination 140 of an initial range of motion. By range of motion, it is meant an examination of a muscle, or group of muscles', ability to traverse a normal, natural path 144. Although fungal infestations, when existent tend to be pervasive and omnipresent, emphasis on an arm range of motions serves the invention best for a handful of reasons. First, arms 142, and the measured appendage 142, tend to be the most naturally movable muscles for most patients 141, unless that patient has sustained an injury particularly targeting the arm in which case we can use neck rotation or hip ROM or straight leg raising. i.e., any muscle that can be tested. Second, the joint between the arm and the body provides a broad range of motions whereby the examiner may choose between one of many pathways. The inventor's preferred basis of examination lies in a planar arm extension ROM 144 from rearward to forward relative to the patient's chest. It is more preferred that the specific range of motion 144 is measured and quantified, as contrasted with a mere qualitative comparison of a before-ROM and after-ROM. Third, the extension of the arms, because of the length of the arm, tends to be exaggerated and easy to measure such that even slight differences in angle change can be detected. As will be explained in greater detail later, the measurements and examinations of an initial-ROM will be contrasted and compared with after-ROM because treatment under the present process not only manifests in an nearly-instant diminishment of fungal pathogen entities actually of 'fungal toxin effect', but also, a nearly-instant return to the natural ROM that the fungal pathogens (toxins) have been (often latently) inhibiting.

In a preferred means of determining a ROM, the health provider can stabilize the scapula while moving arm backwards, and stabilize the opposite shoulder while moving the elbow forward. There can also be a self-test in which the patient stands with straight legs, arm extended out as in the diagram and allow the trunk to twist and arm to reach backward. Notice where the fingers (straight hand with fingers pointing straight out) are pointing to. Then apply an activated preparation or derivative and repeat. This time, if there is neutralization of the fungal toxin, the arm (fingers) will reach further back. The amount of change corresponds to the amount of fungal toxin released or 'present and affecting the muscle tension.'

Determination 102 of fungal infestation can be based on any examination known now, or later devised, in the art. Often these examinations take place via a kit that requires patient fluids that are sent to an external lab for delayed analysis. One of the reasons for the preferred use of the present invention is that fungal infestations can be determined almost instantaneously without necessary recourse to delayed fungal infestation determination kit.

A preparation according to the present invention, and as elsewhere described as being mixed 110 and energized 120, is applied to the patient 130, although there is little-to-no reason to believe that the preparation would not be applicable to any sophisticated organism with a circulatory or nervous system as it has been shown to work on pets/cats, dogs, horses. Any contact with a living cell seems to impart the positive effect. Although this sounds quite broad, inventor evaluations lead to the conclusion that the effects of the preparation on a patient 141 are physical in nature (i.e., not chemical, but a matter of physics) as well as chemical. The application of the preparation to a group of cells results in rapid results not only to the treated cells, but also seems to result in a rapid 'transduction' of the results to nearby cells such that a 'domino effect' of cell rejuvenation occurs. The types of contact 130 that have produced effects are as follows:

Contact with skin. The thinner the skin the better the effect. Slow and modest on thick skin such as palms but virtually instant on thin skin of wrist or back of hand, neck (front) base etc. Most non-invasive hence least reactive form of application. Note that the effect appears to be electrochemical since it is too rapid for circulation (would take approx. 1 minute or more) and there is no neurological mechanism we know of that would explain the rapid effects seen at any part of the body when the substance touches any other part of the body. The effect grossly seems to start immediately and is mostly complete within four seconds! It is interesting that skin is supposed to be non-living cells at the surface yet this still works (hence more support for an electrochemical effect). Also used as eye drops (to relax the ocular muscles and restore better vision), and as eye drops containing methylcellulose as a thickener work better since they last longer on the surface of the eye.

Oral consumption: The oral consumption of spray, liquid or solid (a waxy form like a candle, that is make using a high percentage, eg 10 to 40% of bee's wax) or the powder form in the slow release capsules.

Suppositories. The rectal and vaginal application via suppository has helped prostate/rectal and urinary urgency/vaginal and restored ability to lubricate vaginally after just one application.

Inhalation. The aqueous version of the preparation has been used with effects similar to those of transdermal application.

Injection. Intravenous, intramuscular and subcutaneous injections would mostly correspond to the aqueous forms.

So, subject to application 130 of the active preparation of the present invention to a patient 141, the ROM 144 of the patient 141 with a measurable appendage 142 changes both physically and rapidly. With preparations of the present invention, the existence of fungus, and its treatment, can be determined at the time of examination 102. The use of ROM testing of the arms or legs/hips to see how tight the muscles are can provide an indication of fungal infestation. The testing can be done manually or by a ranger 190 mechanical device, e.g., a swinging platform to rest the arm on. Fungal toxins cause a tightness and restriction of the ROM. This tightening effect is easily reversed via contact with the active preparation. Within four seconds in almost all circumstances the ROM 144 is normalized. A "normal" range-of-motion for purposes of the present invention is a range-of-motion roughly equivalent to the full potential permitted by the joint, tempered by the concerns related to age or non-fungal medication/physical conditions. Because the active preparation of the present invention generally lacks any known other medical/physical benefits, a substantial, near-immediate positive change in range-of-motion is almost certainly based on an immediate destruction of the effects of fungus.

Immediate improvement in ROM suggests the fungal toxin or the effect of the fungal toxin that is causing the muscle tightness is being neutralized. Once the person's fungal burden is reduced, the ROM improvement becomes a constant state without needing the active oil to produce ROM improvement. The level of improvement that we see after treatment, without the application of active oil, roughly corresponds to the level reduction of the body burden of the fungal toxin. Typically, one would expect lower toxin burden reflects lower fungal burden. This is an indirect method of assessing the level of fungal burden in the body. There are blood and urine tests but they are grossly inaccurate because of the tiny amount of fungal toxin it takes to cause a symptom and so many ways the measurements can be distorted. This may be the best way to measure fungal toxic burden. It is biological, not lab instrument driven. It costs little but cannot directly quantify or specify which molds are present or absolute quantity of toxin but can with great accuracy, assess relative toxic burden and show relatively how much of the toxin has been cleared and later, how much returned and how fast. For example, when a patient is cleared using the mold protocol and one or two weeks later they are infected by mold again, it is right to suspect that they are getting re-exposure and getting re-infected, likely based on an environmental hazard. Once the fungal source is located and cleaned, the decreased ROM tends to no longer return (until the next re-exposure).

Figure 9:
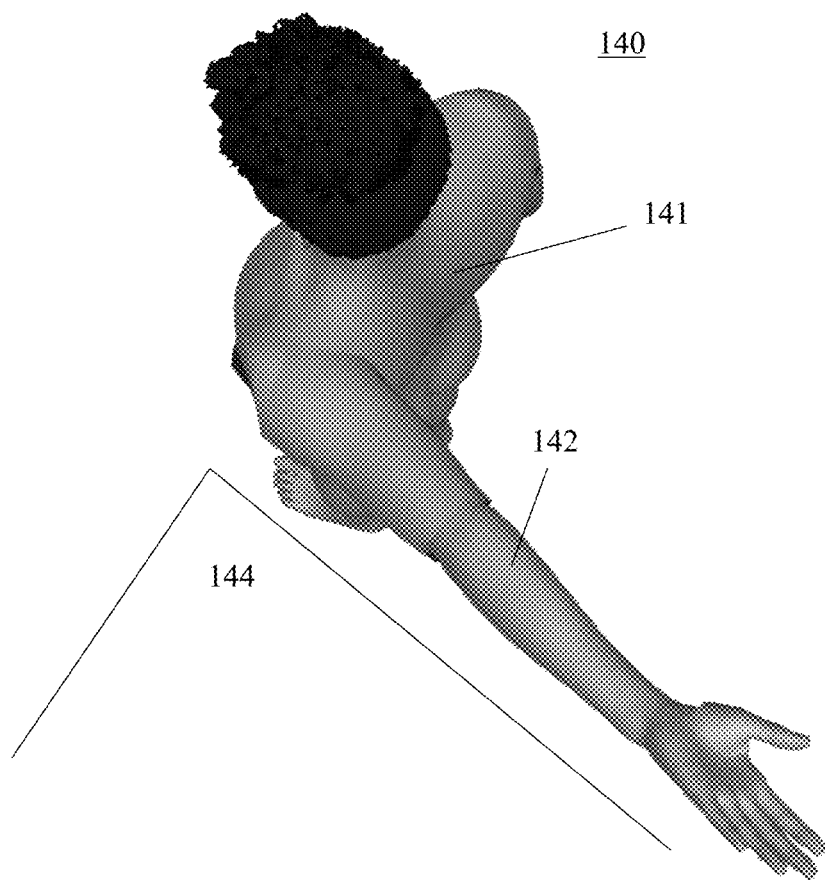
FIG. 9 is a view of range of motion physical examination parameters of the present invention.

The active preparation of the present invention includes the solution or solutions applied to an organism to ameliorate the effects of a mass fungal infestation and the fungal effects. Note that it is likely the case that the active preparation does not directly kill mold, rather it seems to shield from the effects of its toxin. A different part of the patent application that shows how we can deplete the mold's toxin to make it vulnerable to patient white cells or immune defense ameliorates the fungal infection. It is noteworthy that if someone uses the oil daily, often and for long enough, their fungal burden seems to decrease. Perhaps the body can fight off the mold if the toxin is not affecting the immune system as much. In that sense, the oil can ameliorate the fungal burden. The active preparation comes in multiple forms, partially because, the invention began in a rather crude form in order to rapidly be supplied to a patient with little time remaining to seek a cure. However, all of the forms of active preparation described in this document are suitable for the treatments of the present invention, unless otherwise expressly disclaimed. In certain embodiments of the treatment protocol, one version of the active preparation may be more suitable and efficacious than others, and in other embodiments whereby cost and expenses are controlling factors, the cruder forms of the active preparation may still find utility. Turning now to FIG. 9, a process 200 for creating the active preparation 150 of the present invention is shown.

Olives are predominantly used in connection with the active preparation because they seem to have been endowed with natural fungus-fighting chemicals, the exact characteristics of which are not precisely known to the inventor. The olive fruit is a drupe. It has a bitter component (oleuropein), a low sugar content (2.6-6%) compared with other drupes (12% or more) and a high oil content (12-30%) depending on the time of year and variety. These characteristics make it a fruit that cannot be consumed directly from the tree and it has to undergo a series of processes that differ considerably from region to region, and which also depend on variety. Some olives are, however, an exception to this rule because as they ripen they sweeten right on the tree, in most cases this is due to fermentation. One case in point is the Thrubolea variety in Greece. Oleuropein, which is distinctive to the olive, has to be removed prior to commercial sale as an edible fruit, as it has a strong bitter taste. Oleuropein is not, however, known to be detrimental to health. Depending on local methods and customs, the fruit is generally treated in sodium or potassium hydroxide, brine or successively rinsed in water when sold as an edible fruit.

In a conventional-off-the-shelf ("COTS") blender, the inventor has used VITAMIX and BLENDTEC with success, use with a dull blade to liquefy 210 olives. This was easier to do with the dull blade than with a sharp, cutting blade blender. Any other mechanism for grinding or pureeing the olives will also accomplish the task. Place any type of, such as green or brown or black), olives and blend, puree or liquefy. It is found that adding 220 a small amount of olive oil, usually just enough, to cover the top of the olives, makes the blending easier. If done industrially, any mechanism to break down the substance of the olive which can include the pit, and then extract the oil. The solid material was then separated 230 from the liquid oil using a press to extract the oil or a centrifuge to separate the oily substance from the solid and water-soluble component, and then the oil is isolated 240. The oil or oils responsible for the effect can be isolated by fractionating the oil using known standard methods. This extracted oil contains the active ingredients in an oil form, which has been shown to neutralize biotoxins symptomatically. The active substance, which is heat stable to at least 70 degrees Celsius, is then heated 250 to within a range of 48 degrees Celsius to 76 degrees Celsius (about 170 F). The active substance showed strong and rapid loss of effectiveness after being heated above that temperature. The active preparation can then be divided into subunits 260 for dispersal ready for application.

It is significant to note that the less dense olive oil ("light" oil) has a more powerful activity that the total oil of the liquid subset component of the olive oil solution. The isolated solid component was found to have an antagonistic effect that undid the effects of the light oil. Thus the total oil when heated had an effect of relaxing the muscles but because the agonist and antagonist exist together in the natural form, it is easy to see why it was never discovered. In order to see the best effect, the lighter and heavy components of the olive oil must be separated from each other.

Figure 10:
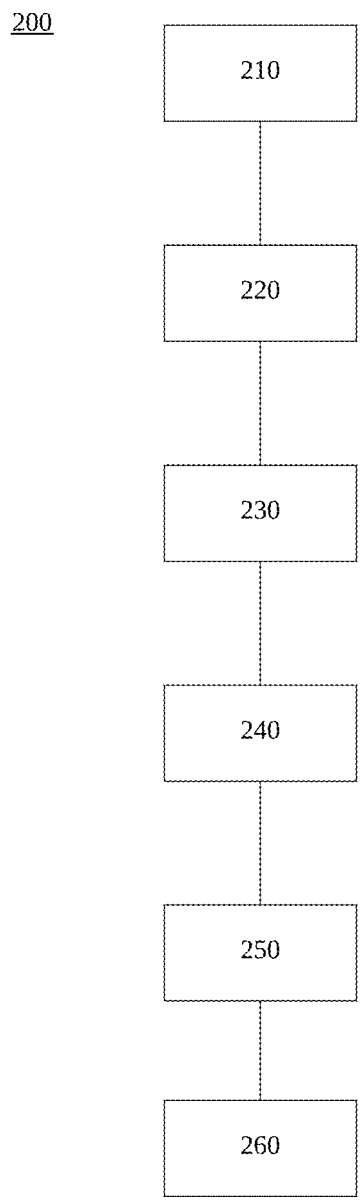
FIG. 10 is a view of an embodiment of a manufacturing process of the present invention.
Figure 11:
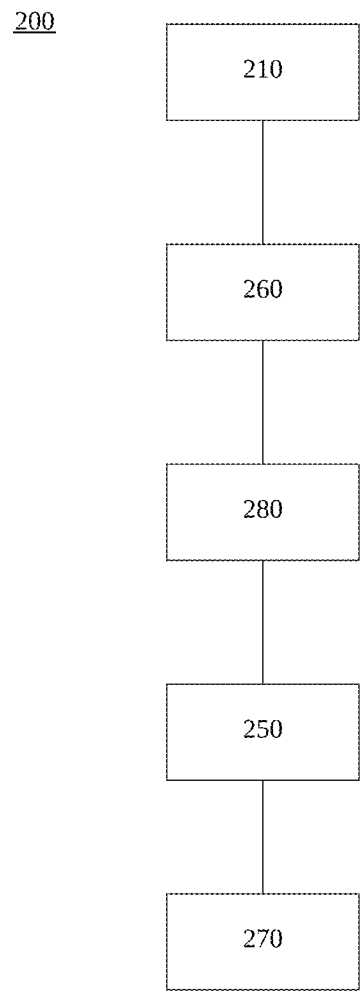
FIG. 11 is a view of an embodiment of a manufacturing process of the present invention.

In FIG. 10, the process 200 of the present invention includes photoexcitation for energizing. The use of photoexcitation to energize and promote electrons within the active preparation 150 results in an energized molecule that achieves the effects of the present application. There is a wide spectrum of frequencies and intensities that work to activate the active preparation, although the primary source of photoexcitation is a 100 W powerful medical laser that activates the olive oil version of the active preparation.

The olive oil version of the active preparation is prepared as discussed above in absent steps related to heating for purposes of excitation. The olive oil active preparation precursor is placed in containers 260 translucent to the frequency of the laser, whereby the translucence was determined by experimental trial and error. One can shine the light through a glass or plastic container that allows the laser light to shine through it. It is preferred that the very same container that is used contain the precursor is the same container that is provided for commercial sale by unit. Experimentation has shown that the distance between the laser source and the container, within practical limits, is not a bar to excitation. However, because the laser light ought to contact the precursor solution within the container, the closer the light the better the result.

The container motioned such that the precursor is continuously agitated 280 for at least the period at which laser excitation 250 is applied to the precursor. By agitation 280, it is meant that that the precursor is motioned by degree that permits displacement of the liquid molecules within the container to ensure that as many molecules as possible are exposed to the photon stream of the laser. The preferred form of agitation includes rotation about a platform, however, other forms of acceptable agitation may include shaking, vibrating, pulsating, stirring, etc. Also, the liquid can be stationary and the laser can move around.

Separating olive oil into the lighter and thicker components with lighter as agonist relaxes muscles and neutralizes fungal toxin effect while the thicker is antagonistic. It is presently believed that the use of infrared (IR) laser on the thicker portions (precipitates when the total solution is cooled), the material becomes an agonist and supports antitoxin effect.

Also, IR laser activates and antagonizes the toxin. Green makes oils antagonistic (muscles become tighter. Blue laser (higher frequency) does this more strongly than green laser. I think yellow was approximately neutral. Thus there are two ways to make the substance antagonistic (by precipitating the heavier molecules and by using high frequency laser). This knowledge may have use on its own (today, might be useful in knowing what to avoid in order to make a more effective energized oil or solution. I think the bottom line is that by using ROM to identify a property, properties can be identified heretofore unseen and unobserved such as the agonist and antagonist effects. We are describing what we can see through the lens of ROM testing, and this is a frame of reference unknown in the prior art. Also, in the treatment of mold, it can be the case that an activated antagonist, eg, Grapefruit seed oil (causes toxin release), can be used, but when light activated, it blunts the ill effects of the toxin. Thus, it is a mold irritant and body protector at the same time.

The excitation 250 by the laser includes a laser that emits a diffuse, non-collimated light rather a narrow beam. This would require either high wattage from a distance sufficient to cover a wide area or low wattage but high time duration. With the laser most frequently used in connection with the present invention, it is found that the beam which exits the laser source is about 2-3 mm diameter and spreads at a distance of about 20 cm such that at the point of contact with the container bearing the precursor, the infrared laser beam has a diameter of about 5-6 cm. To achieve full activation of that region of fluid takes about one to ten seconds from that distance. Spreading can be performed originally from the laser source or by use of a mask to artificially spread the photon stream. The preferred laser is pulsed in order to send pulses of high energy that provide a sufficient amount of energy without the energy stress derived from a constant stream of energy although experimentation has shown that a continuous beam works well too. The pulsing is used for allowing high powered short bursts to not cause tissue damage when used medically. Since the container and oils or other fluids are generally transparent, pulsing is not as necessary in vitro.

Figure 12:
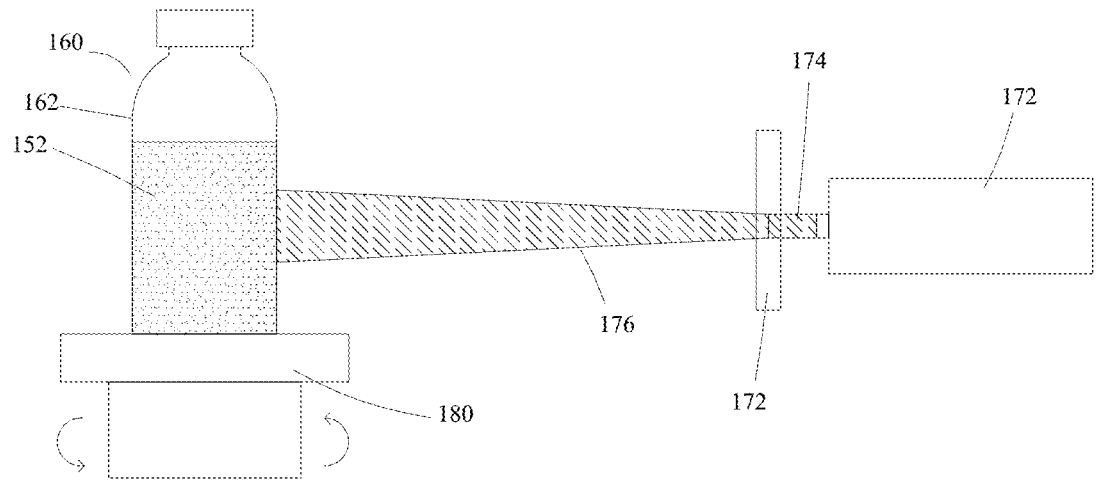
FIG. 12 is a view of an embodiment of a manufacturing process of the present invention.
Figure 13:
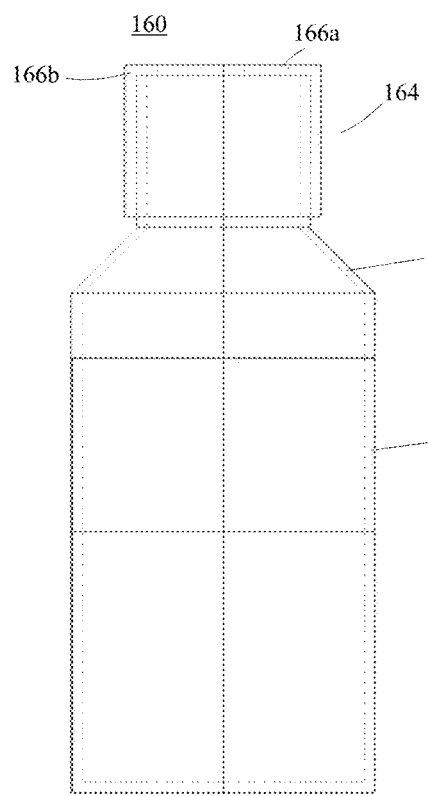
FIG. 13 is a side, exposed view of an embodiment of a container of the present invention
Figure 14:
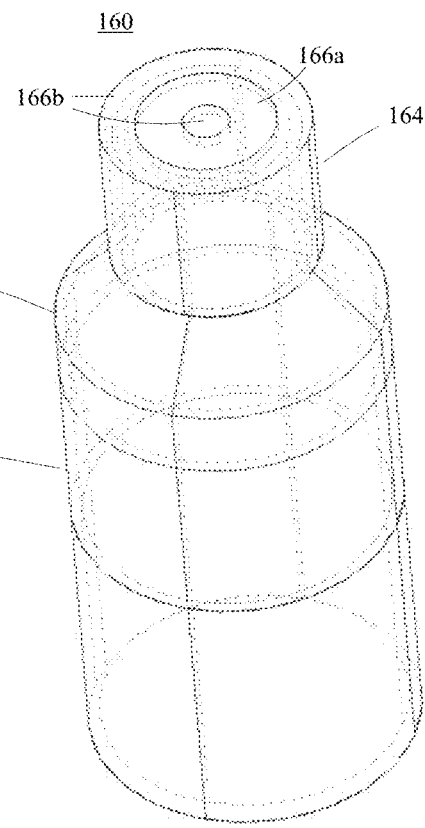
FIG. 14 is a perspective view of an embodiment of a container process of the present invention.
Figure 15:
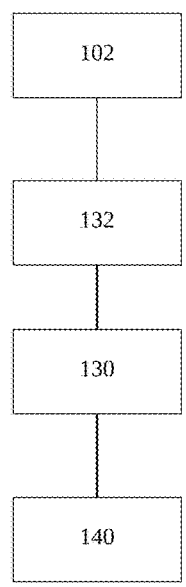
FIG. 15 is a view of an embodiment of a treatment protocol of the present invention.
Figure 16:
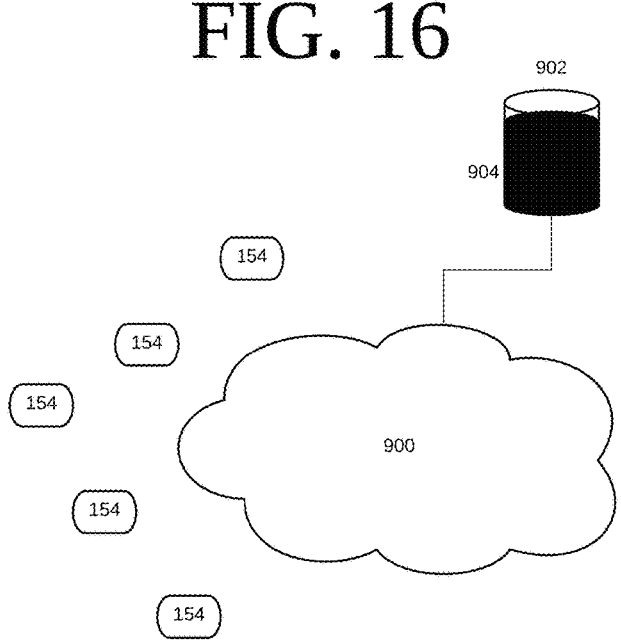
FIG. 16 is a view of a supposed mechanism of the treatment protocol of FIG. 15.
Figure 17:
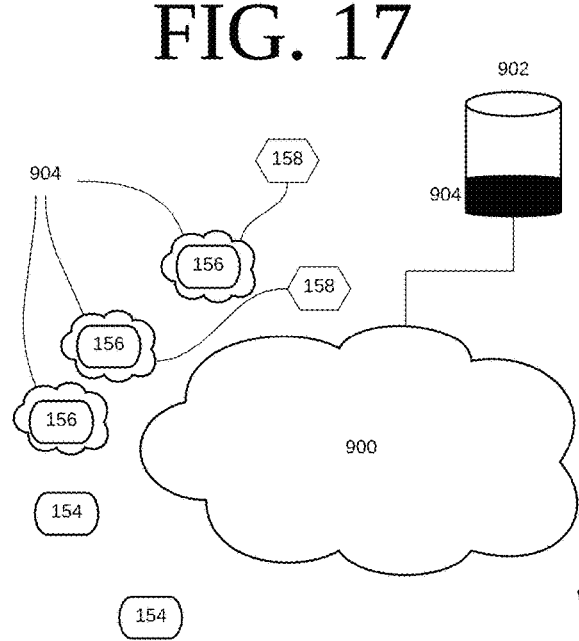
FIG. 17 is a view of a supposed mechanism of the treatment protocol of FIG. 15.
Figure 18:
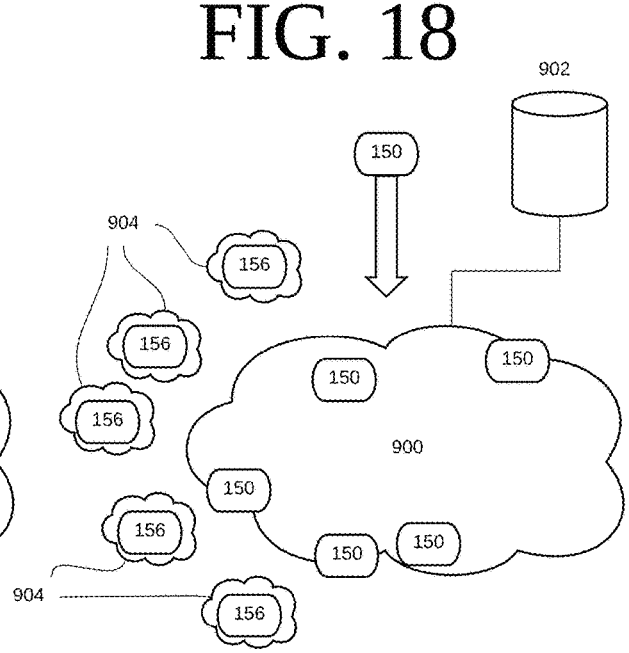
FIG. 18 is a view of a supposed mechanism of the treatment protocol of FIG. 15.

Turning now to FIGS. 12-14, the manufacturing 200 that transforms the precursor preparation 152 in the active preparation 150 is depicted. A container 160 of the present invention includes sidewalls 162 for retention of the precursor 152 as it is transformed to the active preparation 150. The laser 170 includes the lasers as described in this disclosure or any other laser having the attributes suitable to provide the energization as described herein. The laser 170 emits a photon stream 174 that encounters either initially, or as is shown in the depicted embodiment, a mask 172 that diffuses the photon stream into a diverging photon stream 176. The diverging photon stream 176 contacts a translucent sidewall 162a of the container 160 to allow transmittance of the energy of the photons to the precursor 152 within the container 160. The preferred container of the present invention is translucent to the energy transmission of the energy source. In instances wherein the energy source is a laser of predetermined characteristics, particularly frequency and wavelength, the sidewall 162 of the container 106 should have a translucent portion 162(a). By translucent, it is meant translucent to the energy source, irrespective of translucence with respect to the energy available to the environment, e.g. incidental energy provided by, say, ambient lighting. Other portions of the container may include opaque portions 162b. By opaque portions 162b, it is meant that the sidewall portion is opaque to a wide range of common ambient lighting, e.g. the plastic "frosting" or "shading" applied to milk cartons.

The photon streams of the present invention can emanate from any source 170 adapted to provide energy of characteristics suitable to energize the precursor of the present invention to the active preparation. Examples of suitable emission sources for photon streams, coherent or otherwise, may include arc lamps or other gas discharge lamps, or utilize a combination of photon emission sources with suitable filters to select predetermined photon characteristics. The translucent portions 162a of the container 160 may include less than the totality of the container body as it may be preferred to cover the translucent portion with an opaque cover, such as a sticker or hard covering, to protect the internal, sealed active preparation from unwanted environmental energy sources. Furthermore, although translucence is discussed in terms of accessibility to light and photons, because translucence is determined by the ability to permit preferred energy and block unwanted energy, translucence can be based on material properties. An example of a material property unrelated to light translucence includes ray shielding, magnetic shielding, or Faraday caging. Furthermore, portions of the seal 164 may include translucent portions 166a or opaque portions 166b. The terms "opaque" and "translucent" have the same understanding when applied to the cap as when applied to the container body proper.

The substance to be activated, i.e., the precursor substance 152, ideally is a natural oil, e.g., aloe vera gel. Once processed with excessive heat, the substance can no longer be activated with the laser. Substances activated so far include Olive oil, Grape seed oil, Grapefruit seed oil, Castor oil, Aloe Vera gel and juice (aqueous). It is suspected that most natural oils e.g., virgin, may be utilized with the present invention. Processed oils tend not to have the same effect, perhaps because the particulate matter or electrolytes that might be mixed into the oil in natural form are removed in the processing. Plain water does not seem to be capable of transformation to an active preparation but as more electrolytes are added, the longer lasting the effect. Typically, an increase in effect is seen as increased duration rather than an increase in effect.

An agitation source 180 is utilized to supply displacement energy to the container 160 and allow the internal reshuffling of precursor preparation 152 as it is energized to become the active preparation 150. The preferred agitation source or agitator includes a rotating disc that works in conjunction with a container 160 having a translucent sidewall portion 162a. Alternatively, an agitator having an operation similar to a paint shaker may be utilized with the present invention, or during the bottling process, the precursor may be passed through a diverging tube that separates the precursor stream into a wide area for contact with a photon stream prior to convergence on its way into the container.

Returning to FIGS. 1-8, the oil or aqueous forms of the active preparation can be administered topically, orally, by injection or inhaled vapor mist. Solid forms of the active preparation are shown to be effective as well, including when fabricated into slow release capsules using the combined active oils olive, grapeseed, and grapefruit seed. This was mixed with microcrystalline cellulose, which typically used for slow release. The final product looked like a regular dry powder and still had the positive effects of the oils.

Turning now to FIGS. 15-18, the present invention includes an indirect treatment protocol 100 for the treatment of fungal infections comprising a fungicide, including the active preparation 150 of the present invention. The indirect treatment protocol 100, or depletion protocol, includes medicaments significantly broader than the active preparation of the present invention, particularly because the strength of the medicament applied thereto need not conform to the strictures of the active preparation 150. Many fungicides—fungicides defined herein to include any antifungal medication adapted to eradicate or diminish the quantity or quality of fungus contained within an organism—may be utilized with the depletion protocol, and may include Amphotericin B, Various azole derivatives, Echinocandins, Flucytosine, etc.

The indirect treatment 100 can be used in isolation, or in conjunction with any of the range of motion based treatments of this disclosure. A medical practitioner or other professional determines 102 the potential for an illness related to a fungal infection. Fungus has certain defining characteristics and methods of interacting with its surroundings. Of growing interest to researchers is the mechanisms by which fungal pathogens defend themselves. Defense mechanisms used by the fungus *Cryptococcus neoformans* enable it to lead to fatal meningitis, which is one of the opportunistic infections often associated with death in HIV/AIDS patients or in organ transplant recipients, diabetics and other immunosuppressed patients. In doing so, it releases proteins to nullify the activities of the body's defensive macrophages. The immune response is led by macrophages, which circulate in the blood stream and engulf invading microbes to destroy them. The macrophages are essentially tiny defenders for pathogens, using hostile conditions and toxic substances to kill invaders. In this cited case, the pathogen in question released proteins to nullify the macrophages' release of copper, which is toxic to the pathogen. Duke University Medical Center. "Fungus uses copper detoxification as crafty defense mechanism." ScienceDaily. ScienceDaily, 14 Mar. 2013. <www.sciencedaily.com/releases/2013/03/130314141138.htm>

Although the specific mechanisms are not known in minute detail, the present invention relies on natural enemies of fungal pathogens to attack the fungus indirectly. The indirect means of attack goes as follows: (i) expose the fungus to active antagonist 154 entities that the fungus 900 recognizes and for which the fungus habitually releases a limited defense mechanism 904 from a limited defense mechanism supply 902; (ii) trigger the defense mechanism by saturating the area occupied by the fungus thus causing eventual exhaustion of the mold defense/toxin or pulsing the substance noxious to mold until such time as it is believed that the defense mechanism 904 has been exhausted; and then (iii) supply an antifungal medicament 150 calculated to directly attack the fungus 900 when the fungus' ability to defend itself has either been greatly diminished or exhausted. For example, the above-cited fungus defends itself by releasing proteins that inhibit the human body's ability to supply copper to areas inhabited by the fungus, so if an antagonist existed to draw out the fungus' supply of this protein until the fungus maintained no further capacity to manufacture such a protein, it would greatly increase the effectiveness of the direct antifungal medication. As further cited in the very same Science Daily article: "Very few antifungal drugs are effective, so we need to identify the Achilles' heel of these fungal pathogens." Also, we can use this mechanism to exhaust the fungus of the compound that incapacitates the macrophages. The now functional macrophages can attack and kill the fungus.

It has been learned in the course of practicing the present invention that common oregano serves as a highly effective antagonist entity 154. Oregano is variously cited as healthy and unhealthy when dealing with fungus, and the interesting probable answer is that both views are correct. Or rather, it is the case that the initial exposure of fungus 900 to oregano is that the fungus 900 virulently reacts by releasing a toxin calculated to nullify the oregano. So, when a fungal infested body is confronted with oregano, the human body will experience a significant increase in stiffness and pain caused by the release of the toxins by the fungus that nullifies the oregano, making it seem as though the oregano has harmed the body in conjunction with fungus. It is more likely the case that the oregano is not the source of the problem, but rather that the oregano has merely drawn out or caused the release of toxins from the fungus. If, however, the fungal infested body remains exposed 132 to oregano, the fungus begins to have diminished capacity to nullify the oregano, as a nullified antagonist 156, until eventually the fungus exhausts its supply of the toxins 904 that it uses to combat the oregano. Here, the present invention continually supplies 132 the oregano, or other antagonist, until it is demonstrated or believed (from comparative sources, for example) that fungus has greatly diminished its supply of the nullification toxin 904. It is presently unknown from experimentation whether the toxin has been exhausted, or the continued use has diminished the level of toxin to an amount/degree unsatisfactory to combat the oregano. Thus, the experimentation has shown that oregano is only a problem if supplied in an amount insufficient to exhaust the fungal toxin! At this point, either a continued supply or pulsed of oregano can be supplied, or a second, alternative (or combined) medicament 150 can be supplied into the system to attack the fungus. It is shown that the present invention works best by pulsing the oregano by applying a small amount every approximately 45-60 min in conjunction with a substance to oregano or other to diminish the toxic effect of the fungus such as this active oil/cream/balm and/or glutathione. The oregano or other mold noxious substance such as grapefruit seed oil can be applied pulsed or continuously.

Again, the present protocol can rely on the range of motion examination 140 to supplement the present invention. As earlier indicated, the range of motion examination 140 can be initially utilized to determine whether there exists a fungal infection in any degree. As also noted, the release of fungal toxins in response to antagonist results in toxic release that further deteriorates a patient's range of motion; therefore, an earlier indication of fungus can be verified by the application of oregano to a patient whose range of motion, upon subsequent and immediate verification, exhibits greater diminishment. The response to the oregano, and certain other antagonists, is relatively immediate [takes 0.5-1.5 min to observe] and measurable. It is noteworthy that once the fungal burden is minimized, the same oregano given alone does not produce muscle tightness/decreased ROM but instead, tends to support muscle relaxation. Most likely this is due to the body experiencing the beneficial effects of oregano on the body without experiencing the adverse effects of the mold toxin since little or no toxin is released.

Furthermore, and as described in other embodiments, use of the active preparation 150 of the present invention subsequent to the use of the indirect antagonist entities 154 results in immediate relief of muscle and skeletal tension.

Use of medicaments other than those described as the active preparations herein may result in delayed relief.

In a one-day treatment version of the present invention oregano oil is preferably mixed with active oil or oils. Whenever using the oregano containing drops, it can also be applied with a cream consistency as these are slow release, longer acting forms of the oil onto any area of skin and also orally Acetyl Glutathione capsules and oral slow release forms of the activated oils. The creme is to help take the edge off the mold toxin release when an antifungal substance like grapefruit seed oil or Oregano oil is taken. The glutathione is to help break down or detoxify those toxins. One capsule (or more) of the glutathione can be had with each application of activated ingredient, but here the order is important: Glutathione+Creme, then the activated ingredient as a combination of Grape/Grapefruit/Oregano. Glutathione can be given as a cream, orally, skin patch, IM or IV injection.

Then the Grape/Grapefruit/Oregano complex is applied to the body as two to five drops (depending on body size) on skin, times during the day, approximately one hour apart. Thus it is about a 5 hour process. Then take Glutathione one to two capsules first, then apply the slow active oil as a creme or balm in a one inch square but could be more or less. The application of a mold defense neutralizer 158, such Glutathione can occur in the application step 150 of the present invention. The use of the mold defense neutralizer 158 can cancel the ill-effects of the mold toxins, or other mold defense mechanism, which along with the toxins ability to directly affect the antagonist, can also significantly harm the organism receiving the antagonist. The application of the present protocol of the present invention should be carefully applied because the protocol actively results in the release of mold toxins, so the organism should be healthy enough to remain healthy during the protocol or receive the mold defense neutralizer to counteract the mold toxins (or the effects of the mold toxins upon the antagonist).

If the one-day protocol doesn't complete the job of clearing of most of the mold, then these steps can be repeated for another one to five days. To see if it worked, we test ROM as follows:

(1) Baseline ROM (assuming the person tested has not had contact with active oil or cream etc. for about 12+ hours).
(2) If ROM is good (loose muscles) then it is likely the fungal clearing was successful. We then double check by applying a drop of oregano oil onto the skin, rub in and wait 60-90 seconds for the oregano oil to take effect of causing a release of fungal toxins and we then wait for them to reach their target organs. This can be diluted with a neutral oil to reduce skin burn. Also, the oregano can be taken orally, which is significant because topical applications invoke different standards by applicable agencies. This takes 30-90 seconds. If no tightness is observed on testing, then the treatment was successful. If there is (partial) tightness, then the extent to which the treatment was successful is approximately equal to the about of relaxation that remains.
(3) We can then have another check by applying a drop of active oil on skin (or orally etc.) and rechecking ROM. If a residual tightness is relaxed and a full and relaxed ROM is achieved, it shows that there was still some residual fungal toxin effect. Another important aspect of the treatment is that the glutathione can be applied IV intravenously. This is very useful in cases where the patient is very sensitive to the fungal toxin or has impaired detoxification mechanisms. Glutathione is administered IV either as a continuous drip or in a pulsed fashion injected to the IV line or IV solution sped up as needed to counteract fungal toxin effect precipitated but oregano (or other noxious [to the fungus] substance).

Turning now to FIGS. 19-22, the present invention results in a system 310, in vivo or in vitro, having superior treatment attributes. It is believed, and supported by some experimental data, that the mechanism by which the present invention functions utilizes physical means to eradicate fungus from interacting with cell exteriors. One of the means by which fungus 900 is believed to debilitate the human body is by interfering with the life cycle of cells by affixing its toxin(s) like tricothecenes to the cell exteriors or even internal structures. Cell Membrane Destabilization has been studied in relation to fungal toxins in Shank, Roxanne, et al. *Current and Future Experimental Strategies for Structural Analysis of Trichothecene Mycotoxins-A Prospectus*, Toxins, Dec. 2011, 3(12); 1518-1553. Mycotoxins, especially trichothecene are very important. Toxins from trichothecene are implicated in cell membrane destabilization which speaks to the believed results of the activated oils of the present invention.

One of the effects of the use of the active preparations is a significant, but temporary, enhancement in the voltage potential provided by an organism's cellular membrane 312. Cells 300 include a cellular membrane 312 that provides an electrochemical barrier between the cell's interior and the exterior environment of the cell. The cell 300 includes ion channels 320 that allow ions 322 to selectively pass between from inside-out and outside-in. Accordingly, an artificial charge gradient is created that can be used for many life cycle purposes, including communication via cellular synapses—which was an initial means by which it was first discovered that the present invention may be highly related to the quality of the cellular gradient. The introduction of the active preparation 150 to the cell 300, or even the application of the active preparation 150 to a cell 300 in a cellular system 310 energetically contiguous to the cell under observation, results in a likely immediate interference with a fungus' ability to affix to, or inhibit, the cellular membrane's ability to maintain an electrogradient. The increase in cellular membrane voltage potential increases significantly upon application of the active preparation, such that the increase can reach experimentally as high as a 400% increase in voltage potential. More modest gains in voltage potential include increases of 20-100%.

Furthermore, increases in the electrogradient can result in a cellular super state that lasts minutes, days, or possibly weeks. Practical applications indicate that the super state can be relied upon for at least numerous hours per topical application of the activated ingredient of the present invention. If a patient is rife with fungal exposure the superstate can last ten to twenty minutes. If healthy and minimally affected by fungus, the (beneficial) effect can last for days In an unusual set of circumstances, and quite contrary to more orthodox medical situations, the concentration of the activated ingredient of the present invention more strongly relates to the duration of the super state than the intensity of the super state. In practice, with fairly light—almost to the point of infinitesimal—applications of the activated ingredient, the results are maintained, but only briefly. It is believed that such applications have been successful for mere seconds, but with the same activated ingredient, in more dense/concentrated applications (or applications with higher quantities of the activated ingredient) the present invention has been shown to activate a super state of multiple days. Seen more easily with aqueous (vs oil based) solutions, low concentration applied topically can last seconds when applied topically (maybe because it dries out) whereas the same concentration taken orally or as eye drops can last minutes or hours.

Figure 21:
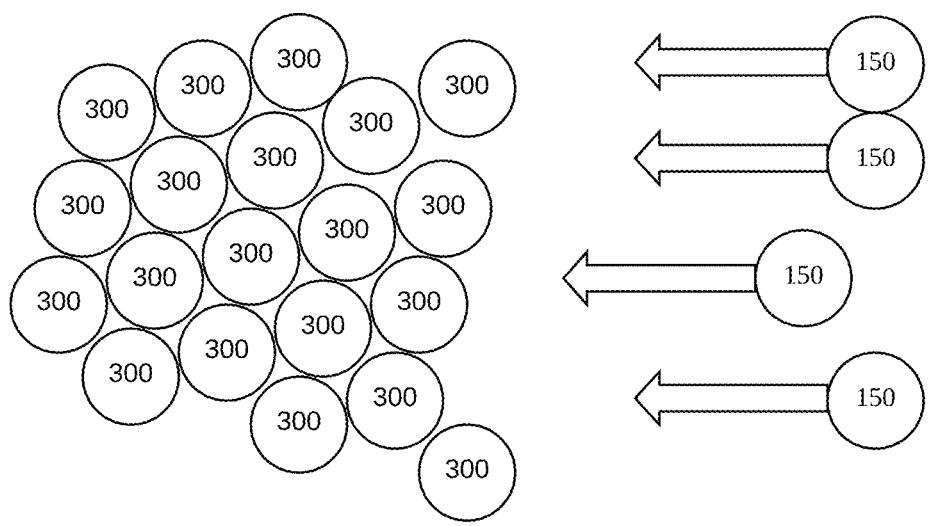
FIG. 21 is a view of an embodiment of a cellular system of the present invention.
Figure 22:
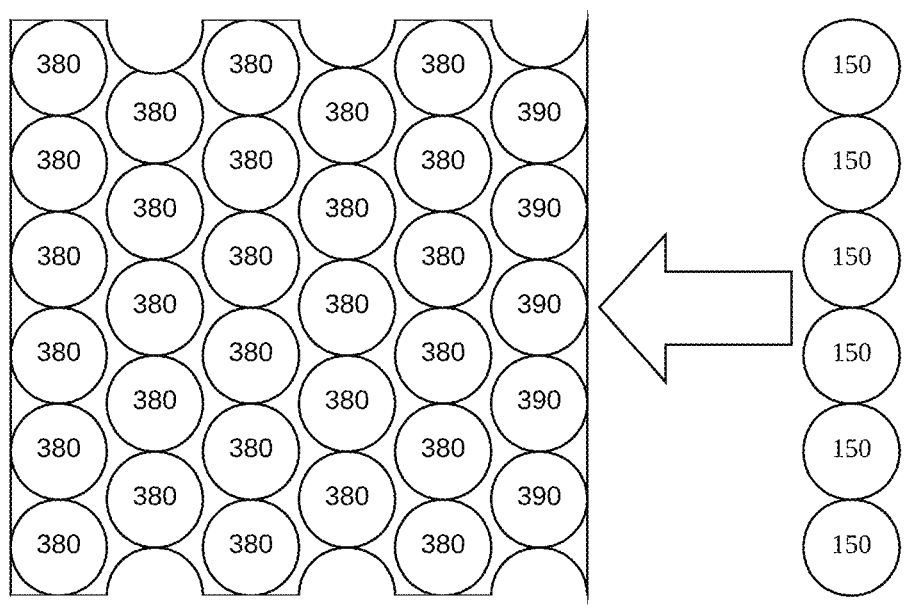
FIG. 22 is a view of an embodiment of a cellular system of the present invention.

The mechanism of the treatment of the present invention does not require direct contact between the fungus-effected cell and the active preparation 150. Whether in vitro (as shown in FIG. 21) or in vivo (as shown in FIG. 22), the present invention requires merely contiguous contact between cells 300. The present invention and its cellular systems 310 can be considered from the standpoint of two cell types, contact cells 390 and linked cells 380. Contact cells 380 are the cells that are directly accessible to the active preparation 150, whereas linked cells 390 are cells that are capable of (i) direct electrochemical contact with contact cells 380 or (ii) direct electrochemical contact with a series of linked cells ultimately in contact with a contact cell 380. The application of the active preparation 150 to the system repairs or enhances to artificially high standards the voltage potential of the cell membranes for all cells linked with the contact cells, as well as the contact cells themselves. In other words, the treatment does not act as an electrical surge whereby the treatment speeds along a path, but rather the treatment acts to treat, and maintain as treated, all cells in the communication pathway for a temporary period of time.

Of significant interest to the observer, the present invention results in the treatment 100 using the active preparation 150 at astonishingly low concentrations of the active preparation 150. Instead, the concentration of the active preparation more greatly affects the duration of the results of the active preparation (for example, the alteration of voltage potential of the cellular membranes within a system 310) such that at dense concentrations, the active preparation can act for hours or days with merely a single dose or at sparse concentrations act for merely minutes. It is unclear why the cellular system 310 reverts to an equilibrium wherein the cellular membrane voltage potential maintains a diminished capacity. It is a likely circumstance that the environment in which an organism operates supplies harmful mold in degree that the human body tolerates and is in continual struggle, and treatment results in a reprieve rather than long-term change in circumstance.

Figure 23:
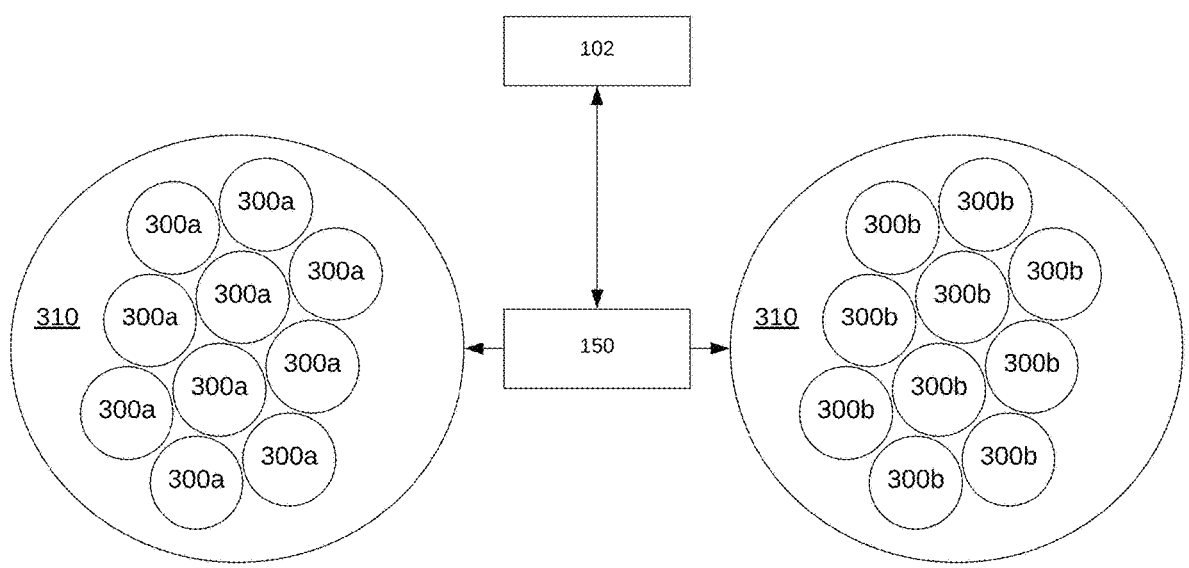
FIG. 23 is a view of an embodiment of a treatment protocol of the present invention.

Turning now to FIGS. 19-20 and 23 the present invention includes a general treatment protocol 100 unrelated to fungus or mold, but rather to the creation of cellular superstate within a system. As previously discussed, the cellular membrane 312 can achieve an unnatural voltage potential based on the application of the active preparation 150. Accordingly, the continued application of the active preparation 130 may result in significant health benefits, including quicker heal times. The patient is diagnosed via a medical evaluation 102 as being capable of benefitting from the cellular superstate, herein defined to include an artificially elevated state of voltage potential based on the application of the active ingredient (and presumably at least the elimination or diminishment of fungal interference with cellular life cycles). The active preparation is applied 150, and then continued to be applied until a desired endpoint based on evaluation 102 of predetermined duration, logical end point, theoretical or observable cure set of circumstances, or the like. The evaluation 102 is preferably revisited throughout the duration of the active ingredient application. The active solution might have a stabilizing effect with regard to other toxins e.g., heavy metals, poisons and other natural substances toxic to us. I haven't researched it but would like to include this possibility if we can.

Although the present invention has been discussed in the greatest clarity that applicant's understanding permits, applicant has sought verification of both the mechanism and results described herein. Applicant gratefully acknowledges the participation of Dr. Gondre-Lewis' research team, as partnered with the Liu Lab, based at Howard University's College of Medicine. The research and experiments performed were done so without benefit of disclosure of the preparation of the active ingredient characterized herein. The experiment by Drs. Gondre-Lewis and Liu (the "Research Team") followed as herein described:

Validation and Efficacy Test

The Research Team was provided with aqueous solutions of the active preparation that readily went into solution when diluted with media. These were labeled 1% and 10% respectively. They were unaware of how the active substance was generated, but it was water-soluble.

The Research Team had access to conventional cell maintenance and preparation equipment. 60,000 Human embryonic kidney 293T (HEK 293T) cells were plated on polylysine coated coverslips for up to 96-120 hours prior to conducting the experiments. HEK cells were incubated in Dulbecco's Modified Eagle's Medium (DMEM) supplemented with 10% Fetal Bovine Serum and 1% PGS at 37 degrees Celsius, 5% $CO_2$ and 95% air prior to starting experiments. The HEK 293T cell culture is widely utilized to investigate the pharmacological actions of drugs and other chemical agents and are maintained in a laminar flow hood. The equipment further included a VWR symphony incubator for cell growth and maintenance, particularly to provide the cells with physiological conditions required for the cells to grow, e.g $CO_2$ as carbonate in the blood and 37 C, the normal body temperature. The equipment included a LAB-CONCO laminar flow hood for passaging cells, including to provide a sterile environment for passaging cells when they are confluent, and for preparing cells prior to the electrophysiology experiment. The examination equipment included an A 1 microscope to permit visualization of the cells for appropriateness of experiments The electrophysiology equipment included a DELL computer for collecting during the experiment for analysis after its completion. Analysis was carried out using ORIGIN and EXCEL software. The Research Team used a Multiclamp 700B amplifier to amplify the electrical signal obtained while recording from HEK cells. An AXON DIGIDATA 1550B—interconnects the multiclamp 700B amplifier and the Dell computer so that protocols can be executed through the computer via installed software known as CLAMPEX or PCLAMP. An AXIOCAM 506 mono provided live video/pictures of the cells during experiments.

Human embryonic kidney 293T cells were plated on coverslips for 96-120 h prior to conducting the experiments. These are epithelial cells, commonly used to test drug activity, but selected by the team because of the potential activation of epithelium hypothesized based on clinical activity, availability, stability and relative ease of use for repeated experiments. HEK cells were incubated in the VWR symphony incubator as discussed above.

For electrophysiological experiments, DMEM was replaced with an external recording solution containing (in mM): 150 NaCl, 5 KCl, 1 $MgCl_2$, 2 $CaCl_2$), 10 HEPES, 10 Glucose (310 mOsm, pH 7.37 with NaOH). Cells were placed in a chamber and bathed in two mL of the external recording solution for the duration of the experiment at room temperature (22-23 degrees Celsius). Borosilicate glass capillaries (3-8 MO) were pulled and filled with an internal recording solution containing (in mM): 158 KCL, 1 $MgCl_2$, 5 EGTA, 10 HEPES (305 mOsm, pH 7.31 with KOH). Membrane potential was recorded with a MultiClamp 700B amplifier (Molecular Devices, Palo Alto, Calif., USA) and low pass filtered at 2 KHz and sampled at 10 kHz with an Axon Digidata 1550B interface using Clampex (V. 11.0.3). Prior to recording, an isolated, unclumped HEK 293T cell was chosen and patched as visualized in FIGS. 27-28.

Isolated HEK 293T cells were chosen as discussed in sections 2 and 3. Cells were visualized with a Microscope equipped with a 40× water immersion lens. Successfully recorded cells were voltage clamped at −50 mV and a baseline recording (120 s to 300 s) was obtained in the external media. After acquiring a baseline, the active preparation solution was ectopically applied via a Gibson P20 pipette to the chamber at a final concentration of 0.1%. In one instance, the unknown drug was applied a second time to a cell making the final concentration 0.2% for that cell. The cells membrane potential was recorded for between ten min to forty minutes following application of the drug (See FIGS. 1A, B, and C).

The dependent variable measured was holding current. Changes in holding current can best be illustrated by Ohm's law. Ohm's law states that shifts in current (I)—NOT HOLDING CURRENT—is a function of both voltage (V) and Resistance (R). Resistance is mathematically defined as the inverse of conductance. See answer to question 6. The equation for Ohm's law is shown below:

$$V=IR$$

Under V-clamp mode, the cell is being held a constant membrane potential (−50 mV). Therefore, if there is any shift in permeability associated with a depolarizing current, the system must pump in hyperpolarizing current to offset that depolarizing current to maintain the cell at a constant membrane potential of −50 mV. The current being pumped in to offset the depolarizing current is called holding current and that is what is being measured (See FIG. 1C). Thus, an elevation in hyperpolarizing holding current suggests the cell is exhibiting elevations in depolarizing current. Elevations in depolarizing current, if voltage was not being held constant, would yield more depolarized membrane voltages as exemplified by Ohm's law.

Figure 27:
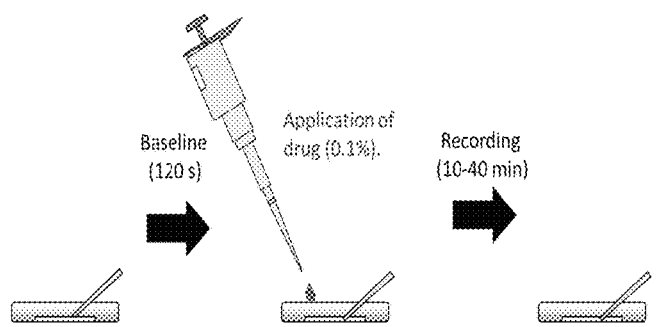
FIG. 27 is a view from a validation experiment based on the present invention.
Figure 28:
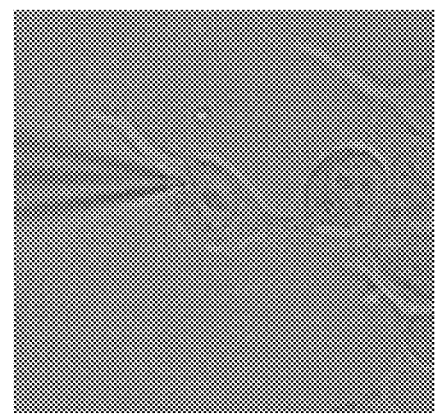
FIG. 28 is a view from a validation experiment based on the present invention.
Figure 29:
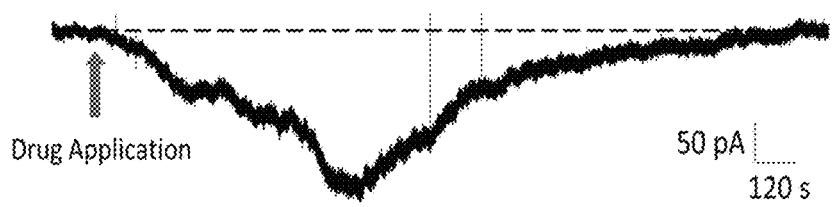
FIG. 29 is a view from a validation experiment based on the present invention.
Figure 30:
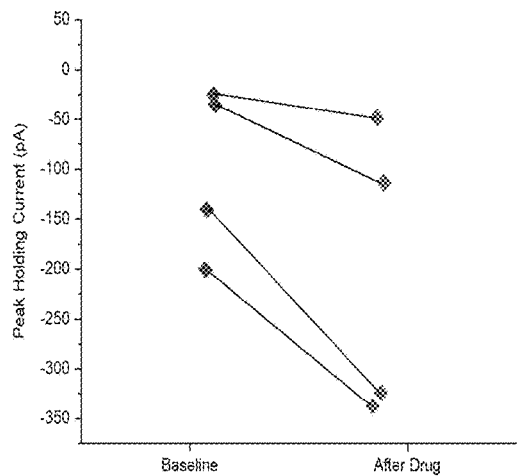
FIG. 30 is a view from a validation experiment based on the present invention.

As shown in FIG. 27, coverslips containing cultured HEK 293T cells were placed in a chamber containing 2 mL of the external media. A single HEK cell was selected, patched, and voltage-clamped at −40 to −50 mV (left). Baseline holding current was measured for approximately 120 s before application of the unknown drug at a final concentration of 0.1% (middle). Holding current was measured for 10-40 min after drug application (right). FIG. 28 is a representative image of a HEK 293T cell being held at constant membrane potential of −50 mV. As shown in FIG. 29, representative trace depicting the effect of the unknown drug on holding current. Drug application induced a slow depolarizing current. This slow depolarization, at the concentrations provided to the Research Team (including its further dilution of the same) reached its maximal peak between 10-15 min following drug application. The cell slowly returned to baseline (dotted line) after drug application. Duration of recording=40 minutes. FIG. 30 is a scatter plot depicting changes in holding current before (baseline) and after drug application. Hyperpolarizing holding current indicates elevated depolarized current within the cell.

As some information was not disclosed to the Research Team, their conclusion were guardedly indicative of the correlation between the active preparation on the alteration of the cell membrane potential. As Dr. Gondre-Lewis explained: shifts in the permeability of ions either in or out of the cytoplasm can cause changes in membrane potential. The factors that could be responsible for this effect are membrane damage or channel alterations. Damage to a cell membrane yields elevations in positive current influx and a very depolarized cell. Shifts in the activation states of ion channels, metabotropic receptors, or transporters can affect ion permeability.

Voltage is a complex component in biological systems and going over the basics of voltage will better illustrate the experiment, its bases, and its conclusions. A cell has a plasma membrane which functionally acts like a capacitor that separates ionic charges of the intracellular environment from the extracellular environment. Acting as a weak conductor itself, the membrane contains biological conductors called ion channels and ion transporters. Conductors allow charge (or ions) to pass through the plasma membrane. The rate by which ions pass through the plasma membrane establishes an ions overall permeability outside and inside a cell. The result is the formation of an electrical circuit by which depolarization and hyperpolarization are mediated by shifts in the permeability of ions through conductors.

This is best illustrated by the mathematical equation known as the Goldman-Hodking-Katz equation. In the GHK equation, the voltage (V) or membrane potential of a cell is a function of the permeability (P) and concentration ([X]) of ions in the cytoplasm (i=inside) and in the extracellular environment (o=outside) of a cell (example ions include $Cl-$, $Ca2+$, $Na+$, $K+$). Resting membrane potential (voltage at rest) can be quite distinct from cell to cell because cells express distinguishable types and amounts of conductors. Thus voltage often exists within a fixed range, rather than a fixed value. Likewise, there is no common voltage differential between distinguishable cell-types. Neurons, for example can have resting membrane potentials as low as −80 mV and as high as −50 mV depending on the neuronal subtype. For cultured HEK 293T cells, non-dividing cells exhibit resting membrane potentials of between −50 to −40 mV. This resting membrane potential is unique to cultured HEK 293T cells.

The Applicant would like to extend its gratitude to the Research Team for providing data and information concerning results and possible mechanisms, namely Marjorie C. Gondre-Lewis, Ph.D, Tomilowo Abijo, Ph.D, Shaolin Liu, Ph.D, and Eric Starr, Ph.D. Their expertise was significant in aiding the Applicant provide the greatest detail available thereto concerning the present invention, but because of the nature of the present invention, it should be noted that these conclusions and results are not conclusive and are based on the information available to Applicant and the research team. The Research Team does not endorse or verify any data within this specification except the data and results that are specifically attributed to them via the experimentation write-up above.

Figure 24:
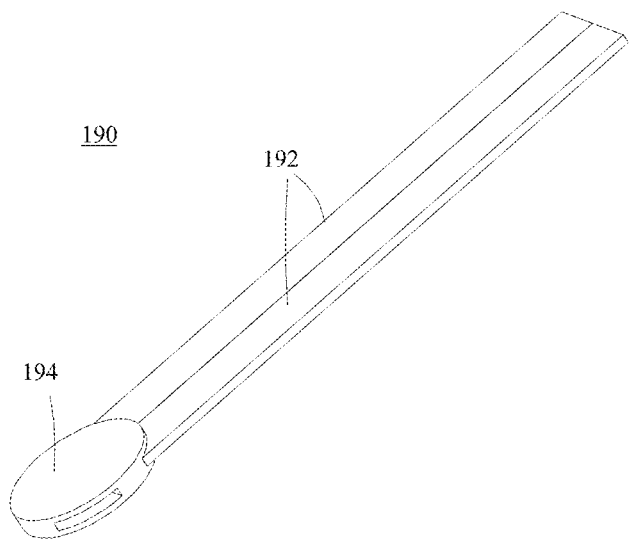
FIG. 24 is a view of an embodiment of a ranger device of the present invention.
Figure 25:
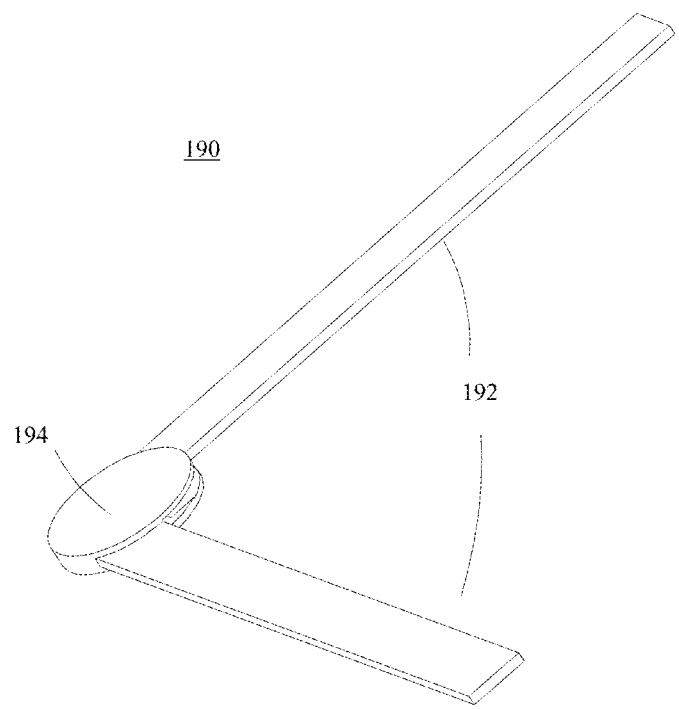
FIG. 25 is a view of an embodiment of a ranger device of the present invention.
Figure 26:
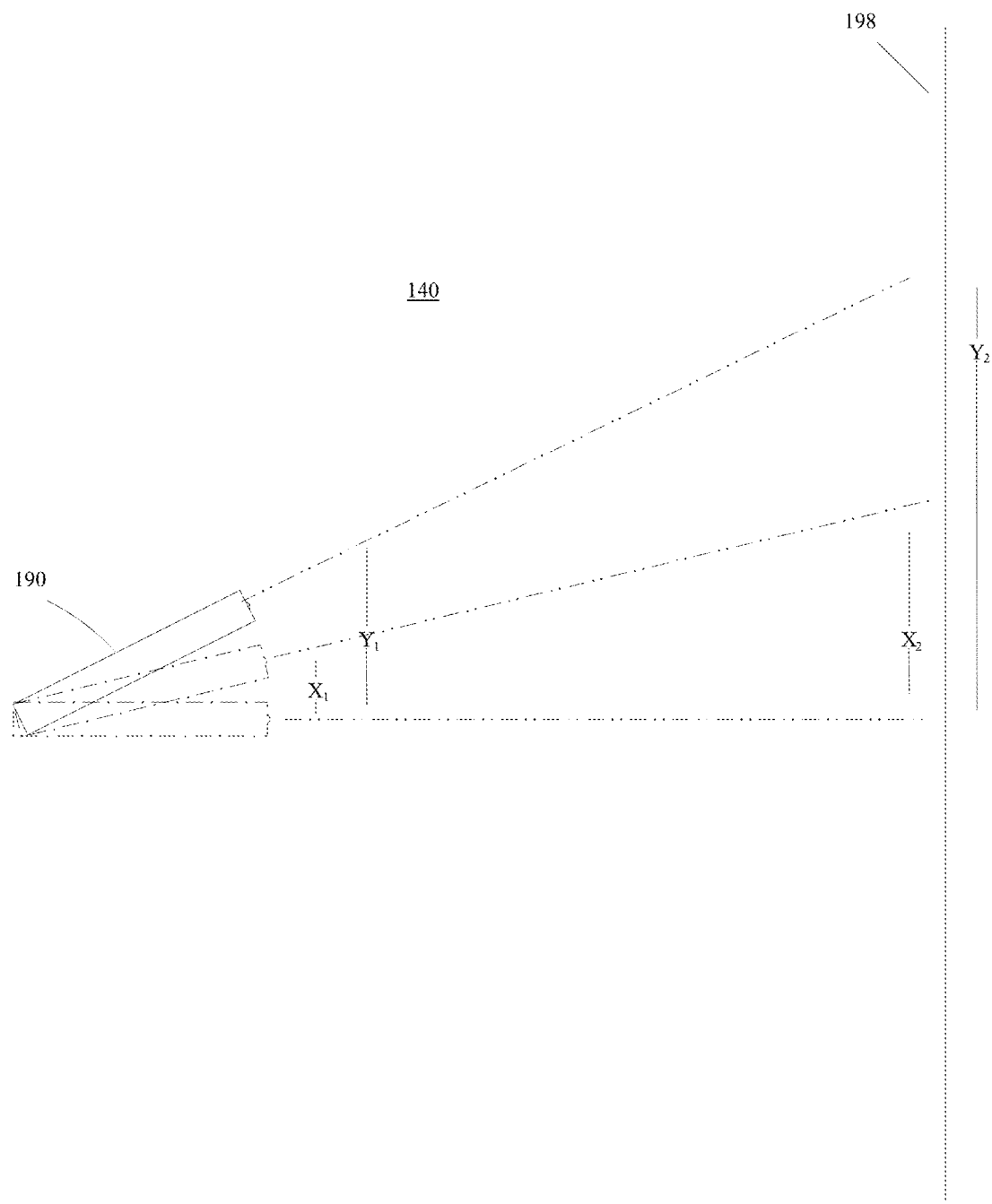
FIG. 26 is a view of an embodiment of a ranger device of the present invention.

Visualization of range-of-motion with a standard organism body may often prove problematic. FIGS. 24-26, when taken with FIGS. 2-9 show how a human, as an exemplary organism, may be supplemented with one or more rangers 190. By range of motion, it is meant an examination of a muscle, or group of muscles', ability to traverse a normal, natural path 144. The range of motion can be naturally detected by eyesight, but as with most pursuits, quantification is preferred. Not only is quantification preferred, but also the ability to exaggerate the extent of ROM can be significant when slight variations in range need to be detected. Applicant has found the use of the exaggerator 190 of FIGS. 24-25 to measure the ROM of patients to be helpful. A ranger 190, for purposes of the present invention, is an any device or process that indicates the position of an appendage (or other measured body part in consideration of ROM) to allow more facile measurement. The ranger 190 shown includes two rotating booms 192 that swivel to illustrate an angle. One benefit of this embodiment is that it may be placed onto the chest of a patient, or back, to allow a patient to rotate an arm inward, and at the ROM extant, the booms will remain in position to prolong the data availability. Even more preferred is the laser ranger 190 that further acts to exaggerate the ROM extents (before and after) of FIG. 26. The laser exaggerator 190 dramatically depicts the change in ROM between a starting extent and later extant, if indeed there is a change. Here, a patient is provided a laser pointer 190 to be held beam-outward. In, for example, the ROM exercise 140 of FIGS. 8-9 the laser 190 would project a spot on the wall indicating the position of a patient arm/hand. The benefit of this exaggeration is that the distance between the starting extent (performed before treatment) and ending extent (performed subsequent to treatment) is significantly magnified. Although the angles remain the same for points $X_1$ and $X_2$ and $Y_1$ and $Y_2$, the apparent distances between $X_1$ and $Y_1$ and $X_2$ and $Y_2$ dramatically differ. Note that although the present invention contemplates an increase in ROM as correlated to an increase in health based on treatment protocols, the purpose of exaggerated measurements is based in accuracy rather than increases for the sake of increases. Elongating the measured entities permits greater confidence in differences. The present invention may utilize any stationary entity 198 for measurement with the laser exaggerator 190. A medical office wall serves as a preferred stationary entity 198 and the wall may be adorned with graduations for the repeated exercise of the present invention, perhaps even with dry-erase coatings.

Although the present invention has been described in considerable detail with reference to certain preferred versions thereof, other versions would be readily apparent to those of ordinary skill in the art. Therefore, the spirit and scope of the appended claims should not be limited to the description of the preferred versions contained herein.

What is claimed is:

1. A method for treating a human infected with black mold and thereby killing the black mold in said human in need thereof, said method comprising:
   a) administering a therapeutically effective amount of a mold antagonist selected from the group consisting of oregano, grape seed oil, and combinations thereof to the human in need thereof;
   b) photoexciting a natural oil selected from the group consisting of drupe oil, fruit seed oil, castor oil, and combinations thereof to an activation energy by applying a laser beam thereto to produce a photoexcited oil;
   c) administering a therapeutically effective amount of said photoexcited oil to the human in need thereof; and
   d) administering a therapeutically effective amount of acetyl glutathione to the human in need thereof to counteract said black mold defense mechanisms in the human in need thereof which effectively kills the black mold in the human in need thereof.

* * * * *